(12) United States Patent
Zhagafarovich et al.

(10) Patent No.: US 7,510,528 B2
(45) Date of Patent: Mar. 31, 2009

(54) DEVICE AND METHOD FOR NONINVASIVE MEASURING GLUCOSE LEVEL IN THE BLOOD

(75) Inventors: Lbaev Arthur Zhagafarovich, Kursk (RU); Urdanov Hussein Bucarvich, Kursk (RU)

(73) Assignee: Shai Shlomo Jaffe, Ramat Gan (IL)

( * ) Notice: Subject to any disclaimer, the term of this patent is extended or adjusted under 35 U.S.C. 154(b) by 791 days.

(21) Appl. No.: 10/941,876

(22) Filed: Sep. 16, 2004

(65) Prior Publication Data

US 2006/0058596 A1 Mar. 16, 2006

(51) Int. Cl.
*A61B 5/00* (2006.01)
(52) U.S. Cl. ..................................... 600/365
(58) Field of Classification Search .......... 600/365
See application file for complete search history.

(56) References Cited

U.S. PATENT DOCUMENTS

| | | | |
|---|---|---|---|
| 5,285,782 A * | 2/1994 | Prosser | 600/324 |
| 6,589,169 B1 * | 7/2003 | Surwit et al. | 600/300 |
| 7,266,400 B2 * | 9/2007 | Fine et al. | 600/316 |
| 2002/0155615 A1 * | 10/2002 | Novikov et al. | 436/149 |
| 2003/0033032 A1 * | 2/2003 | Lind et al. | 700/52 |
| 2003/0153900 A1 * | 8/2003 | Aceti et al. | 604/890.1 |
| 2007/0060812 A1 * | 3/2007 | Harel et al. | 600/347 |

* cited by examiner

*Primary Examiner*—Robert L. Nasser, Jr.
*Assistant Examiner*—Karen E Toth
(74) *Attorney, Agent, or Firm*—Mark M. Friedman

(57) ABSTRACT

A noninvasive blood glucose level measurement system for determining the glucose level of blood, including a processor configured for determining a blood glucose level from a measurement of arterial pressure. Also included is a method of determining a blood glucose level from a measurement of arterial pressure.

30 Claims, 3 Drawing Sheets

DEVICE AND METHOD FOR NONINVASIVE MEASURING GLUCOSE LEVEL IN THE BLOOD

FIELD AND BACKGROUND OF THE INVENTION

The present invention relates to noninvasive medical devices and, in particular, it concerns a noninvasive device for measuring the glucose level in the blood.

By way of introduction, Diabetes is one of the most widespread non-infectious diseases in the world. The occurrence of diabetes has rapidly increased over time, and at the current time, the amount of patients having diabetes in the world has reached 100 million people (about 4% of the world's population). One of the problems in diabetes development is the low awareness of the population about the disease. The amount of registered patients having type II diabetes, which is estimated at 85-90% of the diabetic patients, is 3 to 4 times less than the actual population having the disease. Early diagnosis of diabetes is an important factor in controlling this socially significant pathology and in treating the disease.

A basic diagnostic criterion of diabetes is the concentration of glucose in the blood. Measuring glucose concentration in the blood requires, as a rule, laboratory measurements that involve withdrawal of blood for biochemical analysis. There are instruments that directly measure the glucose level in the blood; however, all of them require the withdrawal of blood from the person.

For people with diabetes, a rapid glucose measurement method is desired since these subjects have to inject insulin several times a day according to the glucose measurement. Additionally, in order for those people to run a normal life style, the measurement and the injection have to be rapid procedures. An example of a device for express measurement of glucose level is the glucometer, which is manufactured by "one touch" in the USA. The measurement of glucose concentration in the blood is carried out by an optical method. The range of the measurement is from zero up to 33.3 mmol/l, with an error of ±20%. The duration of the analysis takes about 45 seconds (according to nameplate data).

Other analogues have been developed, such as the device disclosed in U.S. Pat. No. 5,028,787 to Rosenthal, et al. that teaches quantitative analysis for measuring blood glucose by analyzing near-infrared energy following interaction with venous or arterial blood. Another method using an near-infrared energy analyzer is disclosed in U.S. Pat. No. 6,043,492 to Lee, et al. Another example is disclosed in U.S. Pat. No. 6,091,976 to Pfeiffer, et al. that describes a method for monitoring tissue concentration in which a perfusion solution is conveyed as a liquid column through a microdialysis probe implanted in the tissue and is moved to a test cell preferably arranged outside the patient's body. Other methods and devices are disclosed in U.S. Pat. No. 3,958,560 to March.

The aforementioned devices have two major shortcomings. First, the necessity to withdraw blood using an invasive method involves a trauma factor of the risk of contracting an infectious disease. Second, the accuracy of the devices is insufficient, especially in light of the fact that the amount of injected insulin is determined in many cases from the measurements.

Therefore there is a need to have a noninvasive method for measuring glucose level in the blood. As mentioned herein before, in subjects that have diabetes, the measurement is performed several times a day. In addition, there is a huge population that is prone to the disease for different reasons, such as genetic reasons or bad diet habits, that need to be monitored, but abstain from be monitored due to the need to withdraw blood. More recently, several solutions were proposed and disclosed. An example is disclosed in U.S. Pat. No. 6,721,582 to Trepagnier, et al. which teaches a glucose monitoring instrument based on correlating excitation radiation that is radiated and received at the tissue surface. Another example is disclosed in U.S. Patent Application Publication No. 2003/0,144,582 to Cohen, et al, which teaches receiving information from the skin surface in which an optical coupler allows short-term discontinuous and/or continuous information retrieval on dynamic in-vivo glucose levels. Another example is disclosed in U.S. Patent Application Publication No. 2003/0,233,036 to Ansari, et al. where collimated light is passed through a portion of the eye. Another noninvasive method has been proposed to characterize a particular condition and disease by analyzing the exhaled breath of a person or odor from other parts of a body or from an entity. A shortcoming of the aforementioned systems is that they are not sufficiently accurate enough. A further shortcoming of the aforementioned systems is that they are not convenient to use.

There is therefore a need for a noninvasive device and method for determining glucose levels in the blood which is simple to use.

SUMMARY OF THE INVENTION

The present invention is a noninvasive device for measuring blood glucose level and method of operation thereof.

According to the teachings of the present invention there is provided, a noninvasive blood glucose level measurement system for determining the glucose level of blood, comprising a processor configured for determining a blood glucose level from a measurement of arterial pressure.

According to a further feature of the present invention, the measurement of arterial pressure includes a measurement of systolic arterial pressure and a measurement of diastolic arterial pressure.

According to a further feature of the present invention: (a) the measurement of systolic arterial pressure is an average of a plurality of systolic arterial pressure readings; and (b) the measurement of diastolic arterial pressure is an average of a plurality of diastolic arterial pressure readings.

According to a further feature of the present invention, the blood glucose level is determined such that, the blood glucose level equals $Ae^{BK}$, wherein: A is a constant in the range between 1.77 and 2.02; B is a constant in the range between 0.20 and 0.32, e is the natural logarithm; and K is the measurement of systolic arterial pressure divided by the measurement of diastolic arterial pressure.

According to a further feature of the present invention, there is also provided a display device configured for displaying the blood glucose level.

According to a further feature of the present invention, the display device is further configured for displaying the measurement of arterial pressure.

According to a further feature of the present invention, there is also provided a blood pressure measurement device configured for providing data for the measurement of arterial pressure.

According to a further feature of the present invention, a deviation of the blood glucose level from a conventional biochemical glucose measurement of the blood is less than 5%.

According to a further feature of the present invention, there is also provided a remote device and an interface arrangement, the interface arrangement being configured for outputting the blood glucose level to the remote device.

According to a further feature of the present invention, the remote device is configured to determine at least one of a change of medication and a change of medication dose from the blood glucose level.

According to a further feature of the present invention, the remote device is configured to determine at least one of a change of medication and a change of medication dose from the blood glucose level and the measurement of arterial pressure.

A noninvasive blood glucose level measurement method for determining the glucose level of blood, the method comprising the steps of: (a) receiving a measurement of arterial pressure; and (b) determining a blood glucose level from the measurement of arterial pressure.

According to a further feature of the present invention, the step of receiving is performed by receiving a measurement of systolic arterial pressure and a measurement of diastolic arterial pressure.

According to a further feature of the present invention, there is also provided the steps of: (a) calculating the measurement of systolic arterial pressure as an average of a plurality of systolic arterial pressure readings; and (b) calculating the measurement of diastolic arterial pressure as an average of a plurality of diastolic arterial pressure readings.

According to a further feature of the present invention, the step of determining is performed such that, the blood glucose level equals $Ae^{BK}$, wherein: A is a constant in the range between 1.77 and 2.02; B is a constant in the range between 0.20 and 0.32; e is the natural logarithm; and K is the measurement of systolic arterial pressure divided by the measurement of diastolic arterial pressure.

According to a further feature of the present invention, there is also provided the step of displaying the blood glucose level.

According to a further feature of the present invention, there is also provided the step of displaying the measurement of arterial pressure.

According to a further feature of the present invention, there is also provided the step of taking a blood pressure reading for providing data for the measurement of arterial pressure.

According to a further feature of the present invention, a deviation of the blood glucose level from a conventional biochemical glucose measurement of the blood is less than 5%.

According to a further feature of the present invention, there is also provided the step of outputting the blood glucose level to a remote device.

According to a further feature of the present invention, there is also provided the step of determining at least one of a change of medication and a change of medication dose from the blood glucose level.

According to a further feature of the present invention, there is also provided the step of determining at least one of a change of medication and a change of medication dose from the blood glucose level and the measurement of arterial pressure.

A computer software product, comprising a computer readable medium in which computer program instructions are stored, which instructions when read by a computer, cause the computer to determine the glucose level of blood by performing the steps of: (a) receiving a measurement of arterial pressure; and (b) determining a blood glucose level from the measurement of arterial pressure.

According to a further feature of the present invention, the step of receiving is performed by receiving a measurement of systolic arterial pressure and a measurement of diastolic arterial pressure.

According to a further feature of the present invention, there is also provided the steps of: (a) calculating the measurement of systolic arterial pressure as an average of a plurality of systolic arterial pressure readings; and (b) calculating the measurement of diastolic arterial pressure as an average of a plurality of diastolic arterial pressure readings.

According to a further feature of the present invention, the step of determining is performed such that, the blood glucose level equals $Ae^{BK}$, wherein: A is a constant in the range between 1.77 and 2.02; B is a constant in the range between 0.20 and 0.32; e is the natural logarithm; and K is the measurement of systolic arterial pressure divided by the measurement of diastolic arterial pressure.

According to a further feature of the present invention, there is also provided the step of displaying the blood glucose level.

According to a further feature of the present invention, there is also provided the step of displaying the measurement of arterial pressure.

According to a further feature of the present invention, a deviation of the blood glucose level from a conventional biochemical glucose measurement of the blood is less than 5%.

According to a further feature of the present invention, there is also provided the step of outputting the blood glucose level to a remote device.

According to the teachings of the present invention there is also provided a system for recommending medical treatment based upon a glucose level of blood, comprising: (a) a device configured for determining a blood glucose level; and (b) a processor configured for determining at least one of a change of medication and a change of medication dose from the blood glucose level.

According to a further feature of the present invention, the processor is configured as an adaptive learning system.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a noninvasive device for measuring blood glucose level and method of operation thereof.

The principles and operation of a noninvasive device for measuring blood glucose level according to the present invention may be better understood with reference to the drawings and the accompanying description.

The present invention teaches a unique device and method for determining the glucose level in the blood without withdrawal of blood. The determination of glucose level in the blood in accordance to the present invention is simple and can be performed on a patient in any condition.

Figure 1:
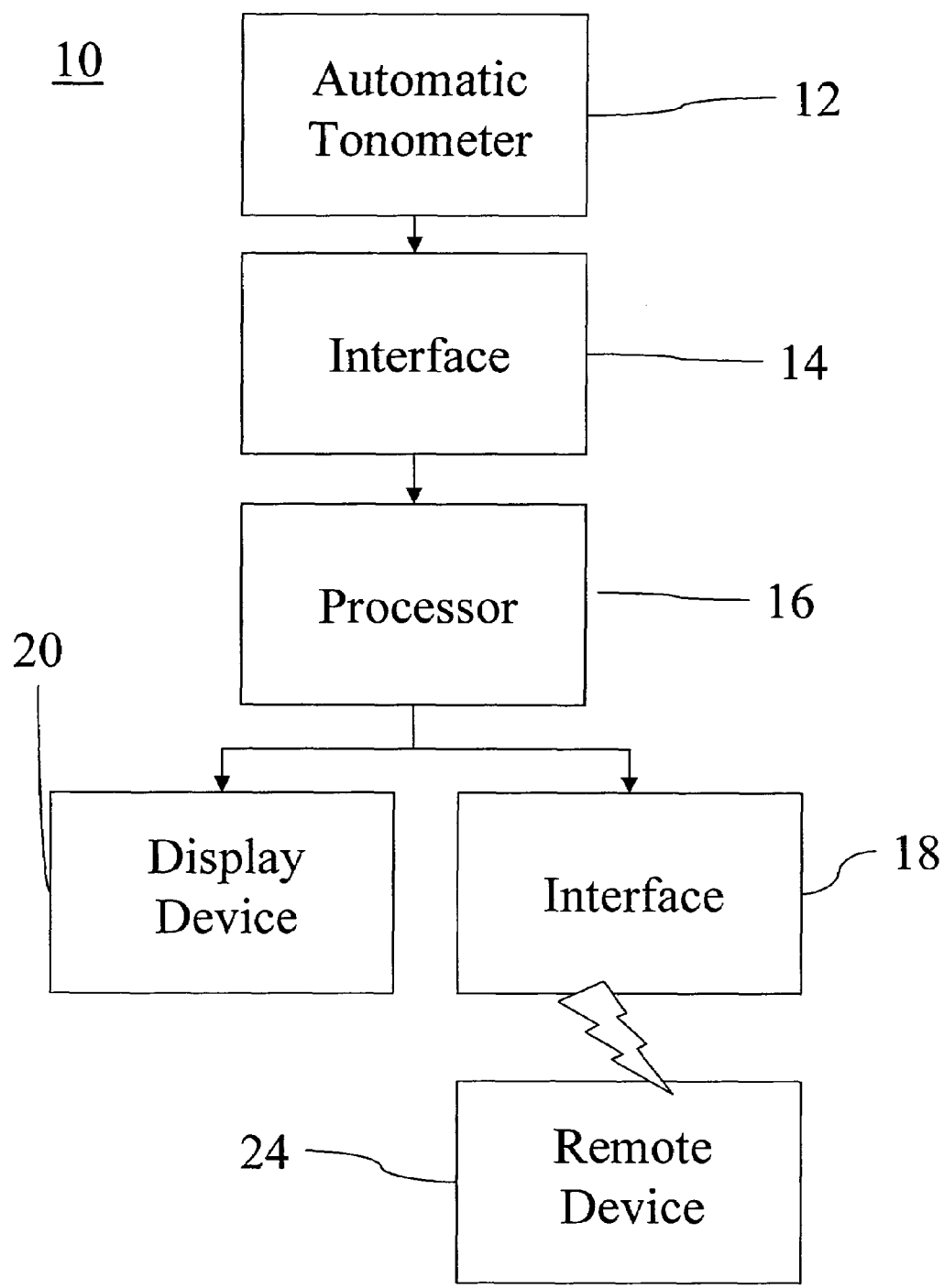
FIG. 1 is a schematic view of a device for determining blood glucose level that is constructed and operable in accordance with a preferred embodiment of the invention.
Figure 2:
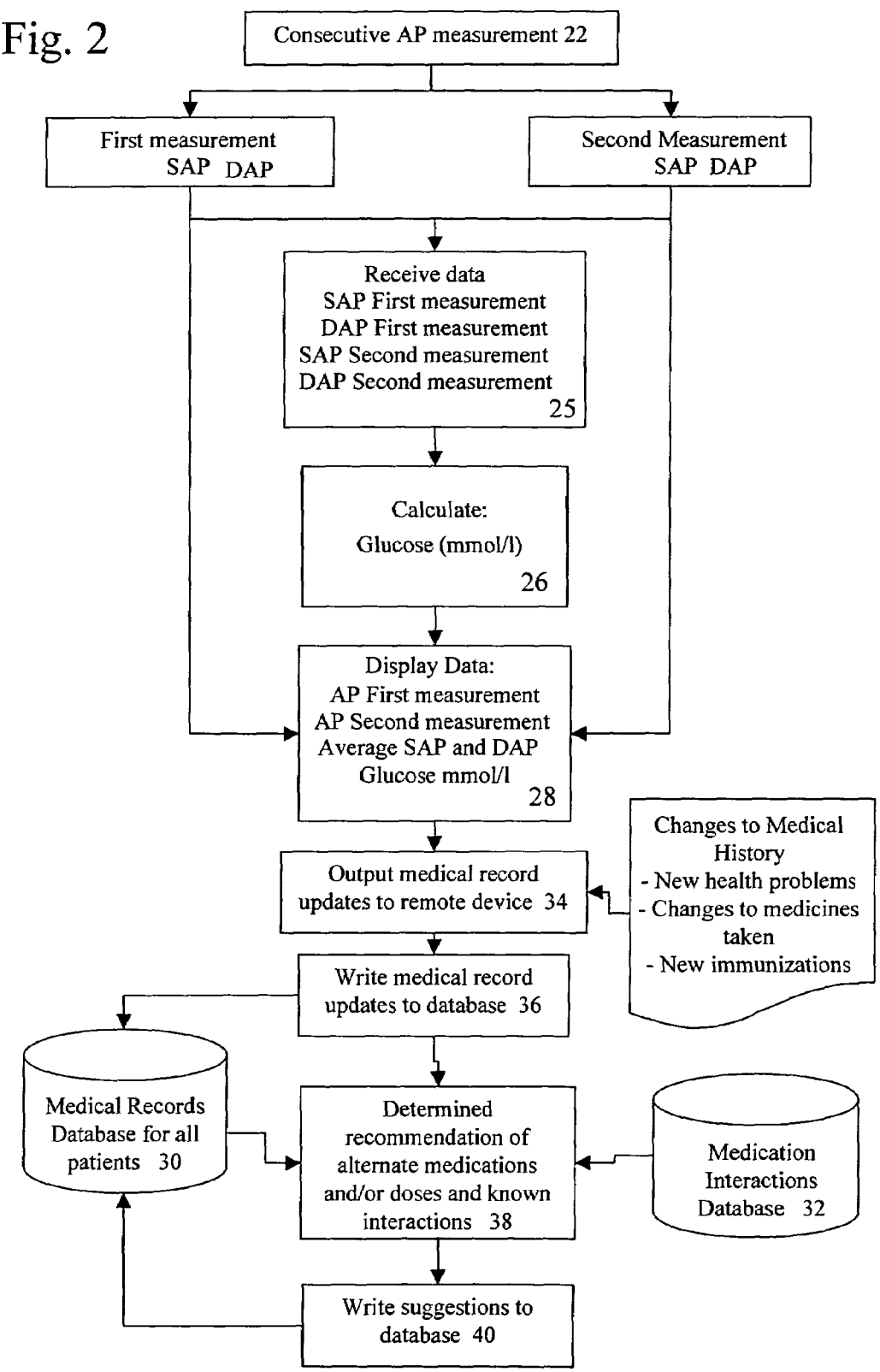
FIG. 2 is a flow chart showing the operation of the device of FIG. 1.

Reference is now made to FIG. 1, which is a schematic view of a system 10 for determining blood glucose level that is constructed and operable in accordance with a preferred embodiment of the invention. Reference is also made to FIG. 2, which is a flow chart showing the operation of system 10 of FIG. 1. By way of introduction, research by the inventors of the present invention showed a correlation between blood glucose level and arterial pressure (AP) measurements. The details of this research are described with reference to FIG. 3. This correlation is therefore employed in system 10 to determine blood glucose level. Therefore, blood glucose level is determined using system 10 by simply taking a blood pressure measurement without needing to take and analyze blood. This has major advantages. First, system 10 enables early detection of diabetes for those who would otherwise not take a glucose blood test. Second, any time a doctor checks blood pressure, the glucose level can also be checked and monitored using system 10. Third, system 10 enables diabetics to test their blood glucose level quickly, in a noninvasive manner and accurately. Clinical tests have been performed using system 10 for four groups of people, including: (a) healthy people and athletes, (b) hypertension patients, (c) diabetic patients and (d) hypertension and diabetic patients. The clinical tests have shown that a deviation of the blood glucose level determined by system 10 from a conventional biochemical blood glucose measurement determined by standard laboratory blood glucose level testing, such as glucose "Exan", is less than 5%. Results of these clinical tests in described with reference to FIG. 3.

System 10 includes a blood pressure measuring device 12, an interface 14, a processor 16, an interface 18 and a display device 20. Blood pressure measuring device 12 is typically an automatic arterial tonometer. A standard automatic arterial tonometer typically has a measurement accuracy of about ±2 mm of Mercury. Blood pressure measuring device 12 is configured to take blood pressure readings for providing data of measurements of arterial pressure including systolic arterial pressure (SAP) and diastolic arterial pressure (DAP). Generally, blood pressure measuring device 12 takes two readings of SAP and two readings of DAP (block 22) on one hand. It will be appreciated by those ordinarily skilled in the art that one reading can be taken on one hand and the second reading on the other hand. It will also be appreciated by those ordinarily skilled in the art that more than two readings of both SAP and DAP can be taken and used in calculations described below. It will be appreciated by those ordinarily skilled in the art that a single SAP reading and a single DAP reading can be taken and used in calculations described below. Processor 16 is operationally connected to blood pressure measuring device 12 via interface 14. The blood pressure readings are transferred by blood pressure measuring device 12 to processor 16 via interface 14. The blood pressure readings are received by processor 16 for further processing (block 25). If blood pressure measuring device 12 is not computerized, it is necessary to input the arterial blood pressure readings into processor 16 manually. Processor 16 is configured to perform the following steps. First, processor 16 averages the SAP readings to give an average SAP. Second, processor 16 averages the DAP readings giving an average DAP. It will be appreciated by those ordinarily skilled in the art that these two steps can be performed in any order. Third, processor 16 determines a blood glucose level, in milli moles per liter, from the average SAP and the average DAP using the following formula (block 26):

$$B=Ae^{BK} \qquad \text{(Equation 1)},$$

where B is the blood glucose level in milli moles per liter, A is a constant in the range between 1.77 and 2.02, preferably 1.9254, B is a constant in the range between 0.20 and 0.32, preferably 0.2623, K is the average SAP divided by the average DAP and e is the Natural Logarithm approximately equal to 2.7182818284. It will be appreciated by those ordinarily skilled in the art that one SAP reading and one DAP reading can be used as input for calculating the glucose level using Equation 1. It will be appreciated by those ordinarily skilled in the art that any of the variables of Equation 1 can be measured and or calculated in different units of measurement and the constants A and B are altered accordingly. For example, B can be calculated in milligrams per deciliter.

It will be understood that processor 16 according to the invention may be a suitably programmed computer, for example, but not limited to using a programming language, such as DELPHI 5 OBJECT PASKAL, which was used by the inventors of the present invention. Likewise, the invention contemplates a computer program being readable by a computer for executing the method of the invention. The invention further contemplates a machine-readable memory tangibly embodying a program of instructions executable by the machine for executing the method of the invention. Display device 20 is configured to displaying the determined blood glucose level, the DAP and SAP readings as well as the calculated average DAP and SAP (block 28). The typical range of blood glucose level determined by system 10 is in the range of 3 to 16 milli-moles per liter. The time taken to determine the blood glucose level of a patient is typically between 45 to 60 seconds, including taking the blood pressure reading using blood pressure measuring device 12. It will be appreciated by those ordinarily skilled in the art that any other computerized or non computerized method of determining blood glucose level using the above method is within the scope of the present invention.

Interface 18 operationally connects processor 16 with a remote device 24. Interface 18 is configured for outputting the determined blood glucose level to remote device 24. Remote device 24 is typically a computer system, PDA or Internet server which stores historical blood glucose level data for use by the patient or the patient's physician.

In accordance with a most preferred embodiment of the present invention, the determined blood glucose level and the measured DAP and SAP are outputted to remote device 24 (block 34). Additionally, details of the current medications taken by the patient (including new immunizations) and current health problems, if different from the last time data was outputted to remote device 24, is outputted to remote device 24. Remote device 24 writes the new data in a database 30 of remote device 24 (block 36). Remote device 24 has two main functions. First, a patient is able to review his medical records stored by remote device 24. Second, the patient receives a recommendation of alternative medications and/or doses as well as medication interactions (block 38). The recommendation is determined by comparing the following factors: (a) the current determined glucose level; (b) the current measured DAP and SAP; (c) the current medication taken; (d) the stored historical medical records for the patient; (e) similar historical medical record data of other patients stored in database 30; (f) a database of medication interactions 32. The step of determining the recommendation is performed in two ways. The first way is to perform the step of determining the recommendation manually by a physician or other qualified technician who uses the historical medical data as a decision-making resource. The recommendation of the physician or technician is then stored in database 30 (block 40). Once enough prior recommendations have been made, the processor of remote device 24 makes decisions by itself using "adaptive learning" technology, without manual input, based upon the prior recommendations of the physician/technician and historical medical data of all the patients. It is known by those skilled in the art of artificial intelligence systems how to design and build a suitable adaptive learning system. The recommendation determined by remote device 24 is then optionally reviewed by a physician or technician before the recommendation is sent to the patient.

Figure 3:
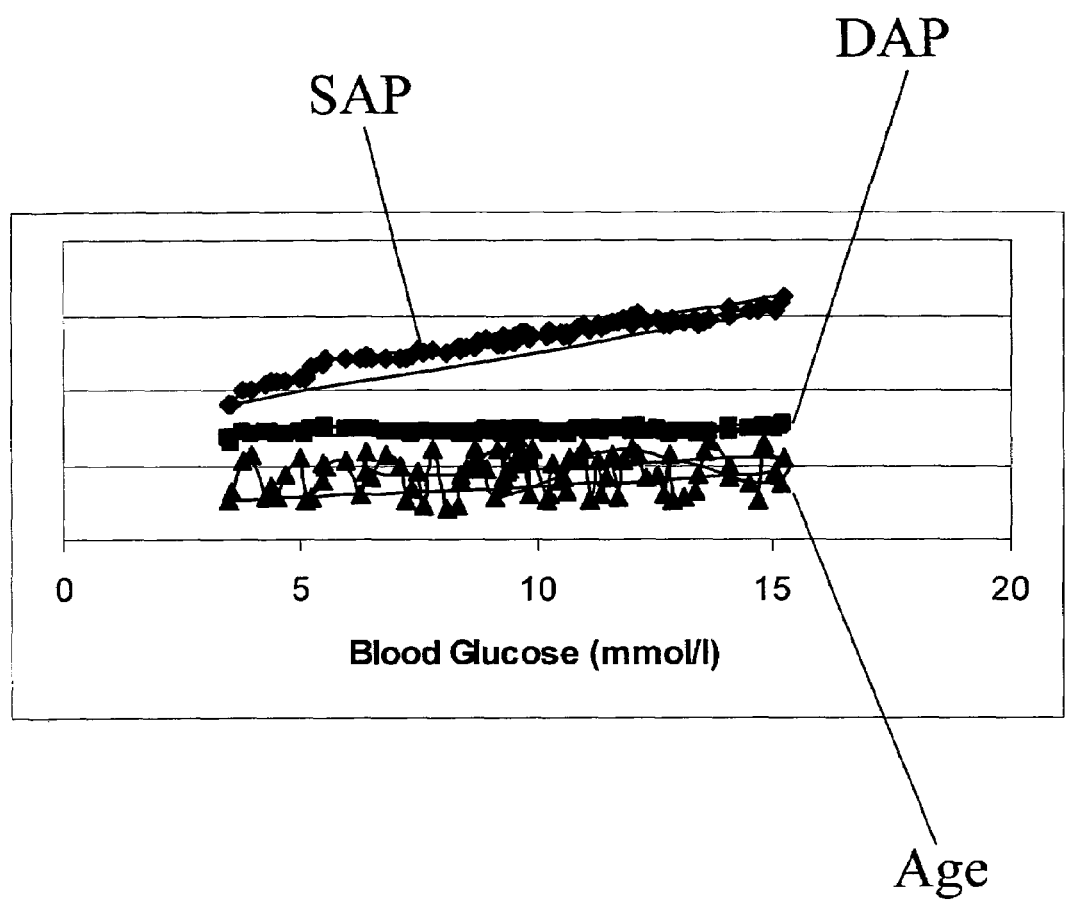
FIG. 3 is a graph showing a correlation between blood glucose level and arterial blood pressure for use with the device of FIG. 1.

Reference is now made to FIG. 3, which is a graph showing a correlation between blood glucose level and arterial blood pressure for 90 diabetics, for use with the device of FIG. 1. Mathematical modeling of the correlation between the level of glucose and the arterial blood pressure was carried out for 90 diabetic patients. The blood glucose level as well as the arterial blood pressure of each patient was measured in the morning after an overnight fasting period. The accuracy of the blood pressure measurements is estimated at about ±2 mm of Mercury. The blood glucose level was measured by removing the patients blood and biochemically analyzing the blood by glucose "Exan" which has an accuracy of ±0.05 milli moles per liter. The average values of the results and their standard deviation are shown in Table 1, below. The linear correlation of the results is shown in table 2.

TABLE 1

| Group Type (sample of 90 people) | Average Age (years) | Average Glucose (mmol/l) | Average SAP (mm Hg) | Average DAP (mm Hg) |
|---|---|---|---|---|
| Diabetics (Type II) | 44.63 ± 12.73 | 9.529 ± 3.154 | 132.478 ± 15.577 | 71.989 ± 1.712 |

TABLE 2

| Dependent variable | Independent variables | Factor of correlation r | Standard Deviation |
|---|---|---|---|
| Glucose (mmol\l) | SAP av. (mm Hg) | 0.9705 | 0.0257 |
| | DAP av. (mm Hg) | 0.4381 | 0.0958 |
| | Age (years) | 0.1843 | 0.1047 |

The correlation between the level of blood glucose and SAP is characterized by high positive factor of correlation (r=0.9705). The correlation between the level of glucose with DAP is less expressed (r=0.4381). There does not appear to be a correlation between the level of glucose and the age of the patients (r=0.1843). The graphic representation shown in FIG. 3 confirms the presence of a distinct correlation between the level of blood glucose and AP.

Table 3, below, shows a comparison between the glucose level measured in a conventional biochemical laboratory by withdrawing blood from the subject and the estimation of glucose level in the blood using system 10. The deviation columns show the difference between the measured and the calculated levels of blood glucose.

TABLE 3

| Sample Number | SAP (mm Hg) | DAP (mm Hg) | Age (years) | Glucose (mmol\l) calculated | Glucose (mmol\l) measured | Deviation (mmol\l) | Deviation (%) |
|---|---|---|---|---|---|---|---|
| 1 | 121.0 | 73.0 | 42 | 6.354 | 6.500 | 0.146 | 2.24 |
| 2 | 120.0 | 72.0 | 56 | 6.477 | 6.800 | 0.323 | 4.74 |
| 3 | 121.0 | 71.0 | 50 | 6.995 | 7.100 | 0.105 | 1.48 |
| 4 | 121.0 | 71.0 | 27 | 7.131 | 7.240 | 0.109 | 1.51 |
| 5 | 122.0 | 70.0 | 34 | 7.410 | 7.360 | −0.050 | −0.69 |
| 6 | 126.0 | 72.0 | 46 | 7.554 | 7.500 | −0.054 | −0.72 |
| 7 | 125.0 | 71.0 | 22 | 7.701 | 7.600 | −0.101 | −1.33 |
| 8 | 126.0 | 71.0 | 60 | 7.850 | 7.820 | −0.030 | −0.39 |
| 9 | 125.0 | 71.0 | 21 | 8.158 | 8.110 | −0.048 | −0.59 |
| 10 | 128.0 | 71.0 | 23 | 8.316 | 8.350 | 0.034 | 0.40 |
| 11 | 127.0 | 70.0 | 40 | 8.478 | 8.400 | −0.078 | −0.93 |
| 12 | 131.0 | 71.0 | 60 | 9.155 | 9.160 | 0.005 | 0.05 |
| 13 | 135.0 | 73.0 | 36 | 9.155 | 9.280 | 0.125 | 1.34 |
| 14 | 130.0 | 70.0 | 41 | 9.333 | 9.330 | −0.003 | −0.03 |
| 15 | 132.0 | 71.0 | 45 | 9.333 | 9.360 | 0.027 | 0.29 |
| 16 | 132.0 | 70.0 | 66 | 9.699 | 9.550 | −0.149 | −1.56 |
| 17 | 136.0 | 72.0 | 68 | 9.699 | 9.600 | −0.099 | −1.03 |
| 18 | 137.0 | 73.0 | 51 | 9.699 | 9.640 | −0.059 | −0.61 |
| 19 | 137.0 | 73.0 | 54 | 9.699 | 9.720 | 0.021 | 0.22 |
| 20 | 138.0 | 73.0 | 55 | 9.887 | 9.800 | −0.087 | −0.89 |
| 21 | 134.0 | 71.0 | 31 | 9.887 | 9.820 | −0.067 | −0.69 |
| 22 | 136.0 | 73.0 | 61 | 9.887 | 9.900 | 0.013 | 0.13 |
| 23 | 135.0 | 71.0 | 27 | 10.079 | 10.200 | 0.121 | 1.18 |
| 24 | 139.0 | 70.0 | 30 | 10.079 | 10.250 | 0.171 | 1.67 |
| 25 | 137.0 | 72.0 | 51 | 10.079 | 10.340 | 0.261 | 2.52 |
| 26 | 138.0 | 72.0 | 40 | 10.474 | 10.500 | 0.026 | 0.25 |
| 27 | 144.0 | 74.0 | 60 | 11.096 | 11.000 | −0.096 | −0.87 |
| 28 | 140.0 | 72.0 | 26 | 11.096 | 11.100 | 0.004 | 0.04 |
| 29 | 143.0 | 73.0 | 52 | 11.311 | 11.300 | −0.011 | −0.10 |
| 30 | 141.0 | 72.0 | 31 | 11.311 | 11.350 | 0.039 | 0.34 |
| 31 | 144.0 | 73.0 | 42 | 11.531 | 11.500 | −0.031 | −0.27 |
| 32 | 146.0 | 74.0 | 56 | 11.531 | 11.610 | 0.079 | 0.68 |
| 33 | 145.0 | 73.0 | 29 | 11.755 | 11.700 | −0.055 | −0.47 |
| 34 | 147.0 | 74.0 | 53 | 11.983 | 11.820 | −0.163 | −1.38 |

TABLE 3-continued

| Sample Number | SAP (mm Hg) | DAP (mm Hg) | Age (years) | Glucose (mmol\l) calculated | Glucose (mmol\l) measured | Deviation (mmol\l) | Deviation (%) |
|---|---|---|---|---|---|---|---|
| 35 | 144.0 | 72.0 | 61 | 12.216 | 12.000 | −0.216 | −1.80 |
| 36 | 153.0 | 74.0 | 38 | 13.975 | 14.530 | 0.555 | 3.82 |
| 37 | 152.0 | 73.0 | 26 | 14.246 | 14.710 | 0.464 | 3.15 |
| 38 | 155.0 | 74.0 | 61 | 14.523 | 14.760 | 0.237 | 1.61 |
| 39 | 157.0 | 75.0 | 65 | 14.523 | 14.820 | 0.297 | 2.00 |
| 40 | 153.0 | 73.0 | 45 | 14.805 | 15.050 | 0.245 | 1.63 |
| 41 | 90.0 | 67.0 | 27 | 3.435 | 3.480 | 0.045 | 1.30 |
| 42 | 90.0 | 65.0 | 32 | 3.501 | 3.540 | 0.039 | 1.09 |
| 43 | 100.0 | 71.0 | 53 | 3.929 | 3.780 | −0.149 | −4.78 |
| 44 | 100.0 | 70.0 | 57 | 4.083 | 4.000 | −0.083 | −2.09 |
| 45 | 104.0 | 71.0 | 29 | 4.326 | 4.300 | −0.026 | −0.60 |
| 46 | 105.0 | 71.0 | 36 | 4.495 | 4.420 | −0.075 | −1.71 |
| 47 | 105.0 | 70.0 | 28 | 4.672 | 4.540 | −0.132 | −2.90 |
| 48 | 106.0 | 70.0 | 43 | 4.762 | 4.700 | −0.062 | −1.33 |
| 49 | 108.0 | 71.0 | 55 | 4.855 | 5.000 | 0.145 | 2.90 |
| 50 | 108.0 | 70.0 | 26 | 5.045 | 5.120 | 0.075 | 1.46 |
| 51 | 110.0 | 71.0 | 27 | 5.143 | 5.150 | 0.007 | 0.14 |
| 52 | 115.0 | 73.0 | 28 | 5.345 | 5.260 | −0.085 | −1.61 |
| 53 | 117.0 | 74.0 | 40 | 5.448 | 5.480 | 0.032 | 0.58 |
| 54 | 118.0 | 74.0 | 51 | 5.554 | 5.500 | −0.054 | −0.98 |
| 55 | 120.0 | 75.0 | 50 | 5.662 | 5.580 | −0.082 | −1.47 |
| 56 | 120.0 | 74.0 | 53 | 5.884 | 6.000 | 0.116 | 1.94 |
| 57 | 121.0 | 73.0 | 30 | 5.998 | 6.260 | 0.262 | 4.19 |
| 58 | 120.0 | 73.0 | 58 | 6.114 | 6.390 | 0.276 | 4.31 |
| 59 | 122.0 | 74.0 | 45 | 6.233 | 6.430 | 0.197 | 3.06 |
| 60 | 129.0 | 70.0 | 43 | 8.642 | 8.420 | −0.222 | −2.64 |
| 61 | 129.0 | 71.0 | 47 | 8.642 | 8.500 | −0.142 | −1.68 |
| 62 | 128.0 | 70.0 | 60 | 8.810 | 8.720 | −0.090 | −1.03 |
| 63 | 132.0 | 72.0 | 52 | 8.810 | 8.760 | −0.050 | −0.57 |
| 64 | 130.0 | 71.0 | 49 | 8.810 | 8.780 | −0.030 | −0.34 |
| 65 | 134.0 | 73.0 | 48 | 8.981 | 8.920 | −0.061 | −0.69 |
| 66 | 133.0 | 72.0 | 29 | 9.155 | 9.140 | −0.015 | −0.17 |
| 67 | 135.0 | 72.0 | 41 | 10.474 | 10.550 | 0.076 | 0.72 |
| 68 | 137.0 | 71.0 | 32 | 10.678 | 10.610 | −0.068 | −0.64 |
| 69 | 135.0 | 70.0 | 55 | 10.678 | 10.700 | 0.022 | 0.21 |
| 70 | 141.0 | 73.0 | 53 | 10.678 | 10.900 | 0.222 | 2.04 |
| 71 | 142.0 | 73.0 | 55 | 10.885 | 10.900 | 0.015 | 0.14 |
| 72 | 150.0 | 75.0 | 60 | 12.216 | 12.020 | −0.196 | −1.63 |
| 73 | 151.0 | 75.0 | 56 | 12.453 | 12.120 | −0.333 | −2.75 |
| 74 | 145.0 | 72.0 | 42 | 12.453 | 12.300 | −0.153 | −1.24 |
| 75 | 147.0 | 73.0 | 44 | 12.694 | 12.550 | −0.144 | −1.15 |
| 76 | 144.0 | 71.0 | 30 | 12.941 | 12.700 | −0.241 | −1.90 |
| 77 | 143.0 | 70.0 | 57 | 13.192 | 12.800 | −0.392 | −3.06 |
| 78 | 147.0 | 72.0 | 27 | 13.192 | 12.900 | −0.292 | −2.26 |
| 79 | 146.0 | 71.0 | 29 | 13.448 | 13.100 | −0.348 | −2.66 |
| 80 | 148.0 | 72.0 | 33 | 13.448 | 13.330 | −0.118 | −0.89 |
| 81 | 144.0 | 70.0 | 43 | 13.709 | 13.400 | −0.309 | −2.31 |
| 82 | 146.0 | 71.0 | 58 | 13.709 | 13.550 | −0.159 | −1.17 |
| 83 | 148.0 | 72.0 | 66 | 13.709 | 13.680 | −0.029 | −0.21 |
| 84 | 155.0 | 75.0 | 49 | 13.975 | 14.050 | 0.075 | 0.53 |
| 85 | 150.0 | 72.0 | 42 | 14.246 | 14.050 | −0.196 | −1.40 |
| 86 | 158.0 | 75.0 | 38 | 14.805 | 15.150 | 0.345 | 2.28 |
| 87 | 162.0 | 77.0 | 55 | 14.805 | 15.200 | 0.395 | 2.60 |
| 88 | 134.0 | 72.0 | 48 | 9.333 | 9.450 | 0.117 | 1.24 |
| 89 | 133.0 | 71.0 | 65 | 9.514 | 9.500 | −0.014 | −0.15 |
| 90 | 135.0 | 72.0 | 53 | 9.514 | 9.520 | 0.006 | 0.06 |

The results of the statistical deviations calculated from the subjects surveyed are shown in Table 4. Table 4 shows that the statistical deviation of values calculated by system 10 compared with the measured glucose blood level does not exceed 5%, a fact that indicates the relatively high accuracy of system 10.

TABLE 4

| Statistical Deviation Type | Statistical Deviation (mmol\l) | Statistical Deviation (%) |
|---|---|---|
| Median | −0.0206908759 | −0.191008967 |
| Min | −0.391990875 | −4.7783646 |
| Max | 0.554834053 | 4.74386062 |

The tests and analysis performed on the above 90 diabetic patients was performed on three other groups, namely, (a) hypertension and diabetic patients, (b) hypertension patients without diabetes and (c) healthy people and athletes. The results of these three groups are shown in tables 5, 6 and 7, below. Table 5 shows the results for the patients with hypertension and diabetes. Table 6 shows the results for the hypertension patients without diabetes. Table 7 shows the results for healthy people and athletes. For each patient in these three groups, the statistical deviation of the blood glucose level calculated by system 10 compared with the measured glucose blood level was less than 1%.

TABLE 5

| Sample Number | Age (years) | SAP Average (mm Hg) | DAP Average (mm Hg) | Glucose Measured (mmol/l) | Glucose Calculated (mmol\l) |
|---|---|---|---|---|---|
| 1 | 28 | 135 | 79.0 | 7.00 | 6.967 |
| 2 | 33 | 138 | 79.5 | 7.32 | 7.325 |
| 3 | 56 | 139 | 79.5 | 7.52 | 7.518 |
| 4 | 47 | 142 | 81.0 | 7.60 | 7.583 |
| 5 | 41 | 140 | 79.0 | 7.85 | 7.868 |
| 6 | 50 | 144 | 80.0 | 8.30 | 8.301 |
| 7 | 37 | 146 | 80.5 | 8.52 | 8.522 |
| 8 | 40 | 145 | 80.5 | 8.32 | 8.321 |
| 9 | 33 | 148 | 81.0 | 8.75 | 8.746 |
| 10 | 51 | 150 | 82.0 | 8.80 | 8.781 |
| 11 | 38 | 152 | 83.5 | 8.70 | 8.705 |
| 12 | 46 | 154 | 83.0 | 9.25 | 9.234 |
| 13 | 60 | 150 | 81.0 | 9.20 | 9.171 |
| 14 | 55 | 156 | 84.0 | 9.25 | 9.265 |
| 15 | 64 | 158 | 85.0 | 9.30 | 9.295 |
| 16 | 59 | 155 | 85.0 | 8.70 | 8.693 |
| 17 | 48 | 159 | 84.5 | 9.73 | 9.724 |
| 18 | 53 | 160 | 82.0 | 11.10 | 11.096 |
| 19 | 55 | 160 | 85.0 | 9.72 | 9.724 |
| 20 | 56 | 163 | 86.0 | 9.96 | 9.970 |
| 21 | 61 | 165 | 87.0 | 10.00 | 9.994 |
| 22 | 65 | 164 | 86.0 | 10.20 | 10.196 |
| 23 | 60 | 168 | 87.0 | 10.66 | 10.678 |
| 24 | 48 | 166 | 85.0 | 11.15 | 11.138 |
| 25 | 39 | 170 | 86.5 | 11.40 | 11.406 |
| 26 | 50 | 172 | 87.0 | 11.65 | 11.665 |
| 27 | 37 | 170 | 86.5 | 11.40 | 11.406 |
| 28 | 26 | 176 | 88.5 | 11.95 | 11.930 |
| 29 | 37 | 172 | 85.5 | 12.45 | 12.467 |
| 30 | 44 | 174 | 86.0 | 12.75 | 12.756 |
| 31 | 43 | 173 | 85.0 | 13.03 | 13.027 |
| 32 | 52 | 178 | 87.0 | 13.32 | 13.318 |
| 33 | 55 | 180 | 87.5 | 13.60 | 13.607 |
| 34 | 36 | 183 | 89.0 | 13.60 | 13.582 |
| 35 | 60 | 185 | 92.0 | 12.46 | 12.471 |
| 36 | 63 | 184 | 90.0 | 13.30 | 13.305 |
| 37 | 39 | 186 | 91.0 | 13.25 | 13.267 |
| 38 | 47 | 187 | 90.5 | 13.85 | 13.849 |
| 39 | 54 | 188 | 90.0 | 14.45 | 14.463 |
| 40 | 66 | 190 | 90.5 | 14.75 | 14.760 |
| 41 | 52 | 196 | 93.0 | 15.02 | 15.017 |
| 42 | 63 | 194 | 92.5 | 14.68 | 14.673 |
| 43 | 67 | 195 | 92.5 | 15.00 | 14.980 |
| 44 | 53 | 198 | 93.5 | 15.30 | 15.285 |
| 45 | 54 | 200 | 93.0 | 16.30 | 16.283 |
| 46 | 42 | 203 | 103.0 | 11.55 | 11.528 |
| 47 | 53 | 200 | 100.5 | 12.00 | 11.960 |
| 48 | 60 | 205 | 102.5 | 12.20 | 12.192 |
| 49 | 56 | 204 | 101.5 | 12.43 | 12.428 |
| 50 | 29 | 205 | 103.5 | 11.75 | 11.747 |

TABLE 6

| Sample Number | Age (years) | SAP Average (mm Hg) | DAP Average (mm Hg) | Glucose Measured (mmol/l) | Glucose Calculated (mmol\l) |
|---|---|---|---|---|---|
| 1 | 36 | 133.0 | 92 | 4.22 | 4.201 |
| 2 | 44 | 135.0 | 93 | 4.25 | 4.249 |
| 3 | 42 | 139.5 | 93 | 4.65 | 4.663 |
| 4 | 53 | 141.0 | 94 | 4.66 | 4.663 |
| 5 | 62 | 144.0 | 94 | 4.95 | 4.959 |
| 6 | 38 | 146.0 | 95 | 5.00 | 5.006 |
| 7 | 30 | 146.0 | 94 | 5.18 | 5.165 |
| 8 | 47 | 148.0 | 95 | 5.24 | 5.212 |
| 9 | 29 | 147.0 | 94 | 5.30 | 5.272 |
| 10 | 22 | 150.0 | 95 | 5.43 | 5.428 |
| 11 | 30 | 151.0 | 96 | 5.40 | 5.365 |
| 12 | 38 | 152.0 | 96 | 5.50 | 5.474 |
| 13 | 29 | 154.0 | 97 | 5.52 | 5.519 |
| 14 | 46 | 153.0 | 96 | 5.60 | 5.584 |
| 15 | 48 | 155.0 | 97 | 5.65 | 5.629 |
| 16 | 57 | 154.5 | 96 | 5.75 | 5.761 |
| 17 | 63 | 156.5 | 97 | 5.75 | 5.742 |
| 18 | 68 | 155.0 | 96 | 5.82 | 5.812 |
| 19 | 55 | 158.0 | 98 | 5.80 | 5.786 |
| 20 | 57 | 158.5 | 98 | 5.85 | 5.843 |
| 21 | 35 | 157.0 | 97 | 5.85 | 5.857 |
| 22 | 29 | 158.0 | 98 | 5.90 | 5.879 |
| 23 | 56 | 159.5 | 98 | 5.90 | 5.901 |
| 24 | 39 | 159.0 | 98 | 5.90 | 5.901 |
| 25 | 66 | 160.0 | 98 | 6.00 | 6.018 |
| 26 | 34 | 159.0 | 97 | 6.10 | 6.094 |
| 27 | 45 | 161.0 | 98 | 6.15 | 6.137 |
| 28 | 49 | 160.0 | 97 | 6.20 | 6.216 |
| 29 | 34 | 165.0 | 100 | 6.22 | 6.222 |
| 30 | 32 | 162.0 | 98 | 6.30 | 6.259 |
| 31 | 40 | 163.0 | 98 | 6.35 | 6.383 |
| 32 | 55 | 162.0 | 97 | 6.45 | 6.467 |
| 33 | 50 | 164.0 | 98 | 6.50 | 6.509 |
| 34 | 39 | 164.5 | 98 | 6.60 | 6.573 |
| 35 | 27 | 165.0 | 98 | 6.70 | 6.638 |
| 36 | 33 | 169.0 | 100 | 6.75 | 6.719 |
| 37 | 43 | 166.0 | 98 | 6.80 | 6.769 |
| 38 | 38 | 167.0 | 98 | 6.90 | 6.903 |
| 39 | 65 | 166.0 | 97 | 7.00 | 7.000 |
| 40 | 56 | 168.0 | 98 | 7.05 | 7.040 |
| 41 | 70 | 170.0 | 99 | 7.10 | 7.079 |
| 42 | 64 | 172.0 | 100 | 7.12 | 7.118 |
| 43 | 55 | 173.0 | 100 | 7.30 | 7.256 |
| 44 | 38 | 175.0 | 101 | 7.30 | 7.293 |
| 45 | 62 | 177.0 | 102 | 7.35 | 7.330 |
| 46 | 58 | 173.5 | 100 | 7.40 | 7.397 |
| 47 | 61 | 176.0 | 101 | 7.44 | 7.433 |
| 48 | 66 | 178.0 | 102 | 7.45 | 7.470 |
| 49 | 54 | 180.0 | 103 | 7.50 | 7.505 |
| 50 | 50 | 175.0 | 100 | 7.55 | 7.540 |

TABLE 7

| Sample Number | Age (years) | SAP Average (mm Hg) | DAP Average (mm Hg) | Glucose Measured (mmol/l) | Glucose Calculated (mmol\l) |
|---|---|---|---|---|---|
| 1 | 18 | 120.0 | 90.0 | 4.22 | 4.201 |
| 2 | 18 | 117.5 | 87.0 | 4.25 | 4.249 |
| 3 | 21 | 121.0 | 89.0 | 4.65 | 4.663 |
| 4 | 20 | 116.0 | 86.0 | 4.66 | 4.663 |
| 5 | 22 | 120.0 | 88.0 | 4.95 | 4.959 |
| 6 | 19 | 110.0 | 80.5 | 5.00 | 5.006 |
| 7 | 25 | 112.0 | 82.0 | 5.18 | 5.165 |
| 8 | 22 | 116.0 | 84.0 | 5.24 | 5.212 |
| 9 | 24 | 118.0 | 85.0 | 5.30 | 5.272 |
| 10 | 26 | 118.0 | 84.0 | 5.43 | 5.428 |
| 11 | 20 | 116.0 | 82.0 | 5.40 | 5.365 |
| 12 | 21 | 115.0 | 81.0 | 5.50 | 5.474 |
| 13 | 20 | 116.5 | 80.0 | 5.52 | 5.519 |
| 14 | 23 | 125.0 | 85.0 | 5.60 | 5.584 |
| 15 | 22 | 120.0 | 80.0 | 5.65 | 5.629 |
| 16 | 21 | 108.0 | 72.0 | 5.75 | 5.761 |
| 17 | 27 | 110.0 | 73.0 | 5.75 | 5.742 |
| 18 | 26 | 124.0 | 82.0 | 5.82 | 5.812 |
| 19 | 28 | 110.0 | 72.0 | 5.80 | 5.786 |
| 20 | 25 | 121.0 | 79.0 | 5.85 | 5.843 |
| 21 | 26 | 110.0 | 71.0 | 5.85 | 5.857 |
| 22 | 24 | 110.0 | 70.0 | 5.90 | 5.879 |
| 23 | 28 | 120.0 | 76.0 | 5.90 | 5.901 |
| 24 | 27 | 112.0 | 70.0 | 5.90 | 5.901 |
| 25 | 21 | 120.0 | 75.0 | 6.00 | 6.018 |
| 26 | 20 | 122.0 | 76.0 | 6.10 | 6.094 |
| 27 | 20 | 122.0 | 75.0 | 6.15 | 6.137 |
| 28 | 21 | 118.0 | 75.0 | 6.20 | 6.216 |
| 29 | 25 | 125.0 | 80.0 | 6.22 | 6.222 |
| 30 | 20 | 124.0 | 80.0 | 6.30 | 6.259 |

TABLE 7-continued

| Sample Number | Age (years) | SAP Average (mm Hg) | DAP Average (mm Hg) | Glucose Measured (mmol/l) | Glucose Calculated (mmol\l) |
|---|---|---|---|---|---|
| 31 | 22 | 121.0 | 77.0 | 6.35 | 6.383 |
| 32 | 24 | 119.0 | 82.0 | 6.45 | 6.467 |
| 33 | 25 | 118.0 | 79.0 | 6.50 | 6.509 |
| 34 | 21 | 125.0 | 77.0 | 6.60 | 6.573 |
| 35 | 22 | 124.0 | 76.0 | 6.70 | 6.638 |
| 36 | 26 | 127.0 | 81.0 | 6.75 | 6.719 |
| 37 | 28 | 116.0 | 80.0 | 6.80 | 6.769 |
| 38 | 24 | 115.0 | 73.0 | 6.90 | 6.903 |
| 39 | 25 | 117.0 | 77.0 | 7.00 | 7.000 |
| 40 | 21 | 123.0 | 76.0 | 7.05 | 7.040 |
| 41 | 20 | 125.0 | 80.0 | 7.10 | 7.079 |
| 42 | 19 | 122.0 | 81.0 | 7.12 | 7.118 |
| 43 | 18 | 114.0 | 80.0 | 7.30 | 7.256 |
| 44 | 18 | 116.0 | 78.0 | 7.30 | 7.293 |
| 45 | 29 | 120.0 | 79.0 | 7.35 | 7.330 |
| 46 | 21 | 118.0 | 76.0 | 7.40 | 7.397 |
| 47 | 24 | 116.0 | 77.0 | 7.44 | 7.433 |
| 48 | 25 | 122.0 | 80.0 | 7.45 | 7.470 |
| 49 | 20 | 126.0 | 81.0 | 7.50 | 7.505 |
| 50 | 24 | 127.0 | 80.0 | 7.55 | 7.540 |

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A noninvasive blood glucose level measurement system for determining the glucose level of blood, comprising a processor configured for determining a blood glucose level from a measurement of arterial pressure.

2. The system of claim 1, wherein said measurement of arterial pressure includes a measurement of systolic arterial pressure and a measurement of diastolic arterial pressure.

3. The system of claim 2, wherein:
   (a) said measurement of systolic arterial pressure is an average of a plurality of systolic arterial pressure readings; and
   (b) said measurement of diastolic arterial pressure is an average of a plurality of diastolic arterial pressure readings.

4. The system of claim 2, wherein said blood glucose level is determined such that, said blood glucose level equals $Ae^{BK}$, wherein,
   (a) A is a constant in the range between 1.77 and 2.02;
   (b) B is a constant in the range between 0.20 and 0.3
   (c) e is the natural logarithm; and
   (d) K is said measurement of systolic arterial pressure divided by said measurement of diastolic arterial pressure.

5. The system of claim 1, further comprising a display device configured for displaying said blood glucose level.

6. The system of claim 5, wherein said display device is further configured for displaying said measurement of arterial pressure.

7. The system of claim 1, further comprising a blood pressure measurement device configured for providing data for said measurement of arterial pressure.

8. The system of claim 1, wherein a deviation of said blood glucose level from a conventional biochemical glucose measurement of the blood is less than 5%.

9. The system of claim 1, further comprising a remote device and an interface arrangement, said interface arrangement being configured for outputting said blood glucose level to said remote device.

10. The system of claim 9, wherein said remote device is configured to determine at least one of a change of medication and a change of medication dose from said blood glucose level.

11. The system of claim 9, wherein said remote device is configured to determine at least one of a change of medication and a change of medication dose from said blood glucose level and said measurement of arterial pressure.

12. A noninvasive blood glucose level measurement method for determining the glucose level of blood, the method comprising the steps of:
   (a) receiving a measurement of arterial pressure; and
   (b) determining a blood glucose level from said measurement of arterial pressure.

13. The method of claim 12, wherein said step of receiving is performed by receiving a measurement of systolic arterial pressure and a measurement of diastolic arterial pressure.

14. The method of claim 13, further comprising the steps of:
   (a) calculating said measurement of systolic arterial pressure as an average of a plurality of systolic arterial pressure readings; and
   (b) calculating said measurement of diastolic arterial pressure as an average of a plurality of diastolic arterial pressure readings.

15. The method of claim 13, wherein said step of determining is performed such that, said blood glucose level equals $Ae^{BK}$, wherein:
   (a) A is a constant in the range between 1.77 and 2.02;
   (b) B is a constant in the range between 0.20 and 0.32;
   (c) e is the natural logarithm; and
   (d) K is said measurement of systolic arterial pressure divided by said measurement of diastolic arterial pressure.

16. The method of claim 12, further comprising the step of displaying said blood glucose level.

17. The method of claim 16, further comprising the step of displaying said measurement of arterial pressure.

18. The method of claim 12, further comprising the step of taking a blood pressure reading for providing data for said measurement of arterial pressure.

19. The method of claim 12, wherein a deviation of said blood glucose level from a conventional biochemical glucose measurement of the blood is less than 5%.

20. The method of claim 12, further comprising the step of outputting said blood glucose level to a remote device.

21. The method of claim 20, further comprising the step of determining at least one of a change of medication and a change of medication dose from said blood glucose level.

22. The method of claim 20, further comprising the step of determining at least one of a change of medication and a change of medication dose from said blood glucose level and said measurement of arterial pressure.

23. A computer software product, comprising a computer readable medium in which computer program instructions are stored, which instructions when read by a computer, cause the computer to determine the glucose level of blood by performing the steps of:
   (a) receiving a measurement of arterial pressure; and
   (b) determining a blood glucose level from said measurement of arterial pressure.

24. The computer software product of claim 23 wherein said step of receiving is performed by receiving a measurement of systolic arterial pressure and a measurement of diastolic arterial pressure.

25. The computer software product of claim 24, further comprising the steps of:
   (a) calculating said measurement of systolic arterial pressure as an average of a plurality of systolic arterial pressure readings; and
   (b) calculating said measurement of diastolic arterial pressure as an average of a plurality of diastolic arterial pressure readings.

26. The computer software product of claim 24, wherein said step of determining is performed such that, said blood glucose level equals $Ae^{BK}$ wherein:
   (a) A is a constant in the range between 1.77 and 2.02;
   (b) B is a constant in the range between 0.20 and 0.32;
   (c) e is the natural logarithm; and
   (d) K is said measurement of systolic arterial pressure divided by said measurement of diastolic arterial pressure.

27. The computer software product of claim 23, further comprising the step of displaying said blood glucose level.

28. The computer software product of claim 27, further comprising the step of displaying said measurement of arterial pressure.

29. The computer software product of claim 23, wherein a deviation of said blood glucose level from a conventional biochemical glucose measurement of the blood is less than 5%.

30. The computer software product of claim 23, further comprising the step of outputting said blood glucose level to a remote device.

* * * * *